US012559579B2

(12) United States Patent
Boetkjaer et al.

(10) Patent No.: US 12,559,579 B2
(45) Date of Patent: Feb. 24, 2026

(54) ENZYMATICALLY MODIFIED GELLAN GUM

(71) Applicant: DuPont Nutrition Biosciences APS, Kongens Lyngby (DK)

(72) Inventors: Kenneth Boetkjaer, Risskov (DK); Lise Stouby, Skanderborg (DK); Graham Sworn, Montlignon (FR)

(73) Assignee: INTERNATIONAL N&H DENMARK APS, Kongens Lyngby (DK)

( * ) Notice: Subject to any disclaimer, the term of this patent is extended or adjusted under 35 U.S.C. 154(b) by 641 days.

(21) Appl. No.: 18/063,849

(22) Filed: Dec. 9, 2022

(65) Prior Publication Data

US 2023/0348632 A1     Nov. 2, 2023

Related U.S. Application Data

(63) Continuation of application No. 16/962,089, filed as application No. PCT/EP2019/050944 on Jan. 15, 2019, now abandoned.

(30) Foreign Application Priority Data

Jan. 16, 2018     (EP) ..................................... 18151777

(51) Int. Cl.

| | |
|---|---|
| *C08B 37/00* | (2006.01) |
| *A23L 29/20* | (2016.01) |
| *A23L 29/269* | (2016.01) |
| *A61K 8/73* | (2006.01) |
| *A61K 31/723* | (2006.01) |
| *C08L 5/00* | (2006.01) |
| *C12P 19/04* | (2006.01) |

(52) U.S. Cl.
CPC .......... *C08B 37/006* (2013.01); *A23L 29/272* (2016.08); *A61K 8/73* (2013.01); *A61K 31/723* (2013.01); *C08L 5/00* (2013.01); *C12P 19/04* (2013.01)

(58) Field of Classification Search
CPC .......... C08B 37/00; A23L 29/20; C12P 19/04; A61K 8/73; C08L 5/00
See application file for complete search history.

(56) References Cited

U.S. PATENT DOCUMENTS

| | | |
|---|---|---|
| 5,190,927 A | 3/1993 | Chang et al. |
| 5,830,734 A | 11/1998 | Christgau et al. |
| 5,994,107 A | 11/1999 | Murofushi et al. |
| 6,037,161 A | 3/2000 | Christgau et al. |
| 6,602,996 B1 | 8/2003 | Sworn et al. |
| 8,231,921 B2 * | 7/2012 | Bezanson ............... C12P 19/04 |
| | | 426/576 |

| | | |
|---|---|---|
| 2003/0010007 A1 | 1/2003 | Wright et al. |
| 2008/0145505 A1 | 6/2008 | Bezanson et al. |
| 2014/0227742 A1 | 8/2014 | Bao et al. |

FOREIGN PATENT DOCUMENTS

| | | |
|---|---|---|
| CA | 2334635 A1 | 12/1999 |
| EP | 526826 A2 | 2/1993 |
| EP | 0526926 A2 | 2/1993 |
| EP | 526926 B1 | 2/1993 |
| EP | 1570843 B1 | 9/2005 |
| JP | 2001-178378 A | 7/2001 |
| JP | 2004-261307 A | 9/2004 |
| JP | 2016-199737 A | 12/2016 |
| JP | 2017-160406 A | 9/2017 |
| JP | 2017-212882 A | 9/2017 |
| WO | 95/02689 A | 1/1995 |
| WO | 99/64468 A1 | 12/1999 |
| WO | 2007-094413 A | 8/2007 |

OTHER PUBLICATIONS

R. Chandrasekaran, et al., "The Crystal Structure of Gellan", Carbohydrate Research, 175, 1-15 (1988).

Remoroza CA, Buchheit HC, Gruppen H, Schols HA, 2014, Descriptive parameters for revealing substitution patterns of sugar beet pectins using pectolytic enzymes, Carbohydrate Polymers, 101:1205-15.

Morris ER, Gothard MGE, Hember MWN, Manning CE, Robinson G, 1996, Conformational and Rheological Transitions of Welan, Rhamsan and Aacylated Gellan, Carbohydrate Polymers, 30 (1996) 165-175.

E.R. Morris et al., Conformational and rheological transitions of welan, rhamsanand acylated gellan, and Carbohydrate Polymers, Elsevier, Feb. 5, 1999, vol. 30, Issues 2-3,165-175.

Nzytech, [online], Pectin Acetyl Esterase 12B, Clostridium thermocellum CtPae12B (CE12), URL<https://www.nzytech.com/en/pectin-acetyl-esterase-12b-clostridium-thermocellum-ce12/>, Publication date : May 2015, [Search date : 2022 to Nov. 2024].

Morrison NA, Clark RC, Chen YL, Talashek T, Sworn G, 1999, Gelatin alternatives for the food industry, Progr Colloid Polym Sci (1999) 114: 127-131.

Chandrasekaran R, Millane RP, Arnott S, 1988a, In Gums and Stabilizers for the Food Industry, p. 183.

Chandrasekaran R, Puigjaner LC, Joyce KL, Arnott S, 1988b, Carbohydrate Research, 181, 23.

Chandrasekaran R, Thailamabal VG, 1990, The influence of calcium ions, acetate and •• glycerate groups on the gellan double helix, Carbohydrate polymers, 12(4):431-442.

Dreveton E, Monot F, Lecourtier J, Ballerini D, Choplin L (1996) Influence of fermentation hydrodynamics on gellan gum physicochemical characteristics, journal of fermentation and bioengineering, 82, 3, 272-216.

Fialho AM, Martins LO, Donval ML, Leitao JH, Ridout MJ, Jay AJ, Morris VJ, Sa-Correia II, 1999, Structures and Properties of Gellan Polymers Produced by Sphingomonas paucimobilis ATCC 31461 from Lactose Compared with Those Produced from Glucose and from Cheese Whey, applied and environmental microbiology, 65, 6, 2485-2491.

(Continued)

*Primary Examiner* — Maryam Monshipouri

(57) ABSTRACT

The present invention relates to process for preparing partially deacylated gellan gum, the process comprising subjecting native or high acyl gellan gum to treatment with an esterase capable of partially deacylating gellan gum.

11 Claims, 5 Drawing Sheets

(56)        References Cited

OTHER PUBLICATIONS

Jaya AJ, Colquhouna IJ, Ridouta MJ, Brownsey GJ, Morrisa VJ, Fialho AM, Leitao HJ, Sa-Correia I (1998) Analysis of structure and function of gellans with different substitution patterns, Carbohydrate Polymers 35, 179-188.

Kool MM, Gruppen H, Sworn G, Schols HA, 2013, Comparison of xanthans by the relative abundance of its six constituent repeating units, Carbohydrate polymers, 98 (2013) 914-921.

E. Topakas, et al., Carbohydrate esterases of family 2 are 6-0-deacetylases, FEBS Letters 584, 543-548 (2010).

* cited by examiner

Fig. 1a

H–(Rha*p*–(1–>3)–β–Glc*p*–(1–>4)–β–Glc*p*A–(1–>4β)–Glc*p*)–H

Fig. 1b

| Repeating unit | $R^1$ | $R^2$ | LA gellan | HA gellan |
|---|---|---|---|---|
| RU1 | Glycerate | Acetate | 0% | 50% |
| RU2 | Glycerate | OH | 0% | 50% |
| RU3 | OH | Acetate | 0% | 0% |
| RU4 | OH | OH | 100% | 0% |

ENZYMATICALLY MODIFIED GELLAN GUM

CROSS-REFERENCE TO RELATED PATENT APPLICATIONS

This patent claims priority as a continuation under 35 USC § 120 to U.S. patent application Ser. No. 16/962,089 (filed Jul. 14, 2020), which, in turn, claims priority under 35 USC § 371 as a national phase of Int'l Patent Appl. PCT/EP2019/050944 (filed Jan. 15, 2019; and published Jul. 25, 2019 as Int'l Publ. No. WO2019/141679), which, in turn, claims priority to European Patent Appl. No. 18151777.2 (filed Jan. 16, 2018). The entire text of each of the above-referenced patent applications is incorporated by reference into this patent.

FIELD OF THE INVENTION

The present invention relates to a process for modifying the structure and functional properties of gellan gum by an enzymatic treatment that changes the level of acyl substitutions. The invention further relates to a partially deacylated gellan gum produced by the claimed process and the use of the partially deacylated gellan gum as an ingredient in food products, pharmaceutical formulations and personal care product.

BACKGROUND OF THE INVENTION

Gellan gum is a microbial exopolysaccharide synthesized by *Sphingomonas elodea* (ATCC 31461). The repeating unit (RU) of the gellan gum polymer is a tetrasaccharide composed of two residues of D-glucose and one of each residues of L-rhamnose and D-glucuronic acid with the following structure [→3)-β-d-Glcp(1→4)-β-d-GlcAp(1→4)-β-d-Glcp (1→4)-α-l-Rhap(1→]. The native polysaccharide is partially esterified; the 1,3-D-Glc residue can be linked to L-glycerate at C-2 and/or to acetate at C-6. A drawing of the chemical structure of a repeating unit of gellan gum with both glycerate at C-2 and acetate at C-6 is shown in FIG. 1*a*.

Gellan gum is a highly effective gelling and structuring agent and has therefore been found attractive for the food industry. Gellan is used at very low concentrations, it gels upon cooling and is known to have a consistent quality and reliable supply due to its manufacture by bacterial fermentation. Gellan gum at low concentrations forms a fluid gel with an apparent yield stress that is highly efficient in suspending particles. In addition, the highly pseudoplastic flow provides a low viscosity at higher shear rates resulting in low effects on mouthfeel. These functions combined makes gellan gum very useful for applications like dairy products, beverages, dressings and sauces.

Gellan gum products are produced commercially in two forms; a high acyl (HA) form resembling the native form expressed by *Sphingomonas elodea*, with an average of 1 glycerate and 0.5 acetate substitutions per repeating unit; and a low acyl (LA) form in which the acyl substituents are completely removed by alkali treatment.

The acyl groups have a profound influence on gel characteristics. HA gellan produces soft, elastic, non-brittle gels, whereas LA gellan produces firm, non-elastic, brittle gels. X-ray diffraction patterns of LA gellan show that it exists in the solid state as a co-axial double helix with 3-fold symmetry (Chandrasekaran et al., 1988a, b). The helical structure of HA gellan was first explored by means of computer modelling to extrapolate from this known solid-state geometry of the deacylated polymer (Chandrasekaran et al., 1990). The main conclusion was that acetate groups lie on the periphery of the helix with no modification of the geometry, but that accommodation of glycerate require a change in the helix geometry. In addition, it has been reported that the glycerate substituents are predominantly responsible for stabilising the helical conformation of gellan gum, leading to the high gelling temperature of HA gellan, whereas the acetate substituents sterically hinder helix-helix aggregation by lying in the periphery of the helix, resulting in soft and elastic gels (Morris et al, 1996).

Even though native gellan gum theoretically contains 1 glycerate and 0.5 acetate substitution per repeating unit, the industrial HA gellan products available contain less than this (approximately 0.8 glycerate and 0.45 acetate per RU, calculated from 22 gellan gum products from 3 different producers, results not published). Native gellan gum is reported to contain about 13% by weight of glycerate groups and about 5% by weight of acetate groups, cf. U.S. Pat. No. 5,190,927. The high effect of acyl substitutions on gellan functionality suggests that even small variations in the acyl level of HA products could be important for application performance.

Discrete structural changes to other hydrocolloids are also well known to influence functionality as exemplified by de-methyl-esterification of pectin which can induce gel formation through so-called egg-box structures mediated by $Ca^{2+}$-bonds. Pectins can have the methylated galacturonic acids in blocks or more randomly distributed, and the degree of blockiness can have a high impact on pectin functionality and thus how pectin behaves in a food system (Remoroza et al., 2014).

Previously, different approaches have been undertaken to obtain variable levels of gellan gum acylation. Chemical deacylation of gellan gum by treatment with weak bases is disclosed U.S. Pat. No. 8,231,921 B2 and CA 2334635, Morrison et al. (1999) and Morris et al. (1996). Differences in the acylation level of gellan gum have also been carried out by modifying conditions during fermentation, for instance by using changes in dissolved oxygen tension or growth medium composition (Fialho et al. (1999) and Dreveton et al., (1996)).

U.S. Pat. No. 5,190,927 discloses a method of partially deacylating gellan gum resulting in gellan gum with low levels of acetate residues (0-1% by weight), but retaining some or most of the glycerate residues (3-12% by weight). After fermentation of *S. elodea* to produce native gellan gum, the pH is adjusted with KOH at 25-40° C. for 6-18 hours followed by decreasing the pH to 6-8. The resulting partially deacylated gellan gum is reported to be able to form elastic, non-brittle gels.

Also, genetic changes to the production microorganism have been employed as a strategy to modify the final level of gellan acylation (US 2003/100078 and Jaya et al. (1998)).

A wide range of gel textures can be produced through blends of HA and LA gellan gum. However, it has been demonstrated that mixtures of the HA and LA forms exhibit two separate conformational transitions at temperatures coincident with the individual components (Morrison et al. 1999).

The acetate substitution is known to affect the interaction between gellan helices. When acetate is present, it interferes with interhelical aggregation by sterically blocking ion-mediated interaction. In contrast, acetate contribute very little to the formation and stability of individual gellan helices, which is mainly affected by the presence of glycerate (Morris et al., 1996). Removing acetate specifically would therefore provide gellan intermediates that retain the high stability of individual helices providing high gelling temperatures due to unchanged glycerate levels, but with low acyl gellan properties in terms of interhelical interactions affecting properties such as thermal hysteresis.

The high specificity of acetate removal by enzymes is shown in the present invention where a gradual removal of acetate is obtained by enzyme PAE12B while the glycerate content is retained at approximately 100% of control. Only with treatments at high temperatures (70° C.) and for long incubation times (20 hours), glycerate is partly removed. This glycerate removal is also seen in samples incubated at the same conditions but without enzyme. This shows that the glycerate removal is not mediated by the enzyme. When chemical deacylation is carried out, choosing specific conditions for the alkaline treatment has been shown to allow some specificity towards the removal of either glycerate or acetate (EP0526926 and Morris et al 1996). However, this specificity is not as complete as it is with the enzymatic deacylation. In EP0526926 examples 2, 3 and 4 acetate is removed specifically using low temperatures during alkaline treatment. However, the starting level of glycerate is about 11.3% and is reduced to about 9% during the alkali treatments. This reduction is about 20% of the starting glycerate level, and shows that the chemical deacylation is not as specific as what can be obtained using the enzymatic method of the present invention.

An object of the present invention is to provide gellan gums with intermediate acyl levels and desired stability to obtain products that possess a single conformational transition and therefore behave as a single ingredient.

SUMMARY OF THE INVENTION

Esterases acting on pectin are known to possess different mechanisms of action, such as random or blockwise de-esterification, which in turn provides modifications of pectin that have very different effects on functional properties. During the research leading to the present invention, the inventors assumed that esterases acting on gellan might possess similar types of difference in the mechanism of action which could result in additional functional properties of gellan intermediates obtained through enzymatic de-acylation.

Gellan gum produced as HA or LA gellan represents two counterpoints of gel textures, and partially deacylated gellan gum could therefore potentially provide intermediate gel textures with a wide range of properties. Being able to control the level of acylation might make it possible to make gellan gums with tailor-made setting temperatures and rheological properties, ideally providing one hydrocolloid for all gel textures. Tailoring the molecular structure of gellan gum to the specific functional needs of various food applications the present invention may provide a range of new products. These products may be used individually or combined into blends for various food systems.

With intermediately acylated gellan gum a wide range of textures, from hard and brittle to soft and elastic, can be achieved leading to a range of functionalities in food systems with one versatile hydrocolloid ingredient. The value of this has been shown by Morrison et al. (1999) in which textural properties of gelatin was closely matched by partially deacylated gellan gum.

A different approach to the above described strategies for generating intermediately acylated gellan gum is to employ an enzymatic treatment. By using high acyl native gellan gum treated with an esterase that can specifically remove acetate and/or glycerate groups from the polymer, it is possible to modify the level of acyl substitutions. An enzymatic removal of acyl groups is likely to be more easily controlled compared to chemical de-acylation. For instance, it may be possible to remove only the acetate groups or only the glycerate groups by appropriate selection of the enzyme unlike the chemical treatment disclosed in U.S. Pat. No. 5,190,927 which results in removal of both the acetate groups and some of the glycerate groups. In addition, enzymatic deacylation may create other types of deacylation patterns, such as blockwise deacylation. Furthermore, enzymatic deacylation has been found not to affect the polymer length of gellan gum significantly as can be the case with chemical deacylation. Molecular weight is important for gel strength and texture, and an enzymatic approach may therefore generate new types of high molecular weight low acyl gellan gum with beneficial properties.

Accordingly, the present invention relates to a process for preparing partially deacylated gellan gum, the process comprising subjecting native or high acyl gellan gum to treatment with an esterase capable of partially deacylating gellan gum.

In another aspect, the invention relates to partially deacylated gellan gum which has a molecular weight that is less than 10% reduced compared to the molecular weight of native gellan gum.

In a further aspect, the invention relates to a food product comprising an enzymatically modified, partially deacylated gellan gum as described herein.

In a still further aspect, the invention relates to a pharmaceutical formulation comprising an enzymatically modified, partially deacylated gellan gum as described herein.

In a still further aspect, the invention relates to a personal care product comprising an enzymatically modified, partially deacylated gellan gum as described herein.

As appears from the schematic illustration below (FIG. 2), low-acyl gellan gum (LA) and high-acyl gellan gum (HA) are placed at either extreme on the scale of gel textures, whereas other gel-forming hydrocolloids are in between. Being able to create intermediately acylated gellan gum by the present process may provide the option of spanning the whole range of textures with one hydrocolloid and offer unique rheologic properties not available with the current portfolio of hydrocolloids.

BRIEF DESCRIPTION OF THE DRAWINGS

The invention is further described with reference to the drawings in which

Figures 1A, 1B:
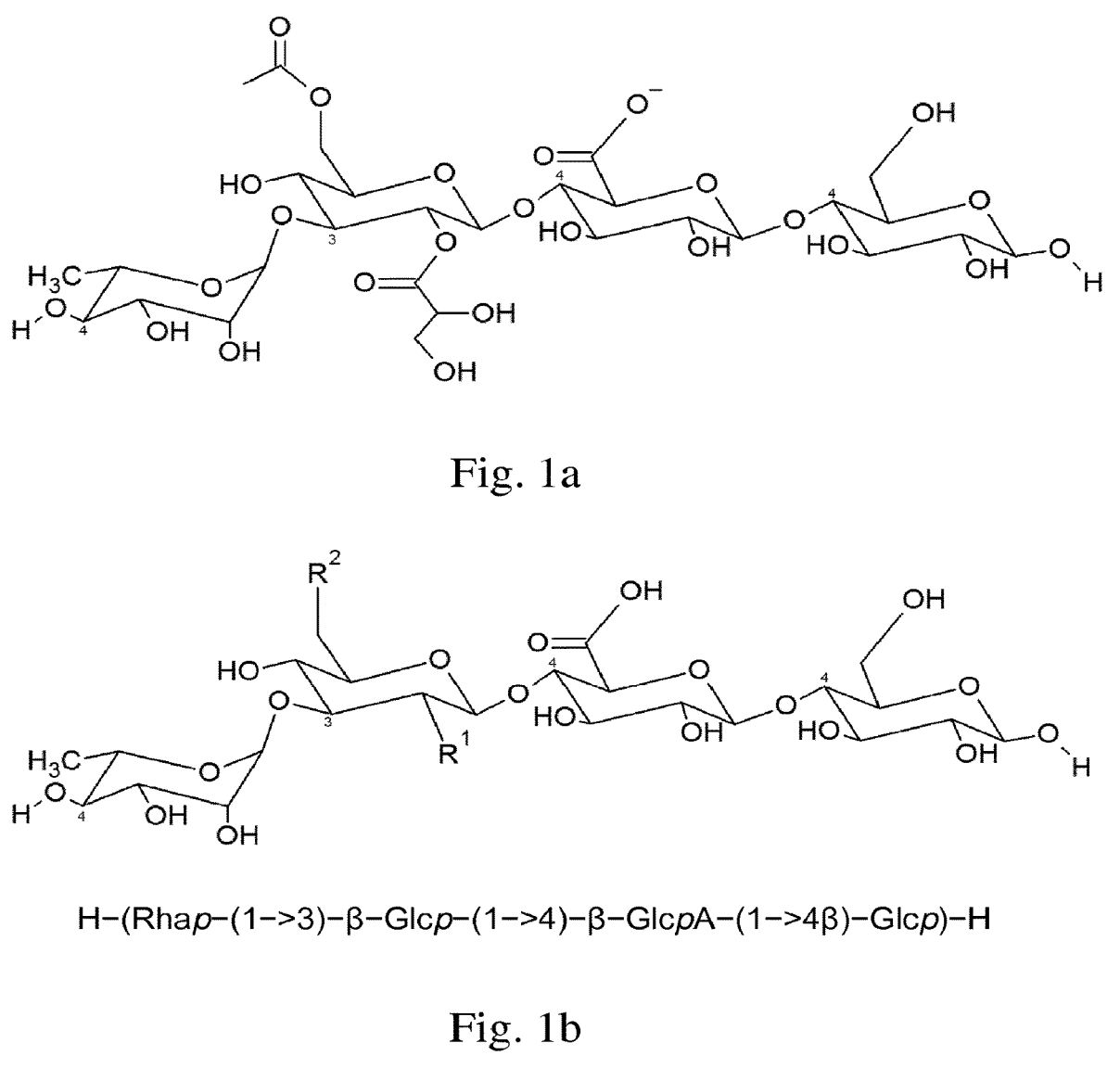

FIG. 1a shows the chemical structure of a repeating unit (RU) of high acyl gellan and indicates the location of acetate and glycerate substituents. The order here from left to right is rhamnose, glucose, glucuronic acid and glucose. The glucose which is α-bound to the reducing end of rhamnose has acetic acid ester bound to the C-6 position and glyceric acid bound to the C-2 position. FIG. 1b shows the same chemical structure as FIG. 1a, except that $R^1$ may be either hydroxy or glyceric acid and $R^2$ may be either hydroxy or acetic acid.

FIG. 1c is a table showing the composition of the four different RUs occurring in gellan gum with respect to the acylation pattern (presence of glycerate and/or acetate groups in HA gellan and LA gellan, respectively).

FIG. 2 is a schematic illustration of the gel textures of gels made from different hydrocolloids, from soft and flexible gels made from high acyl gellan gum to firm and brittle gels made from low acyl gellan gum with gels made from other hydrocolloids ranging in between.

DETAILED DESCRIPTION OF THE INVENTION

Figures 1C, 2:
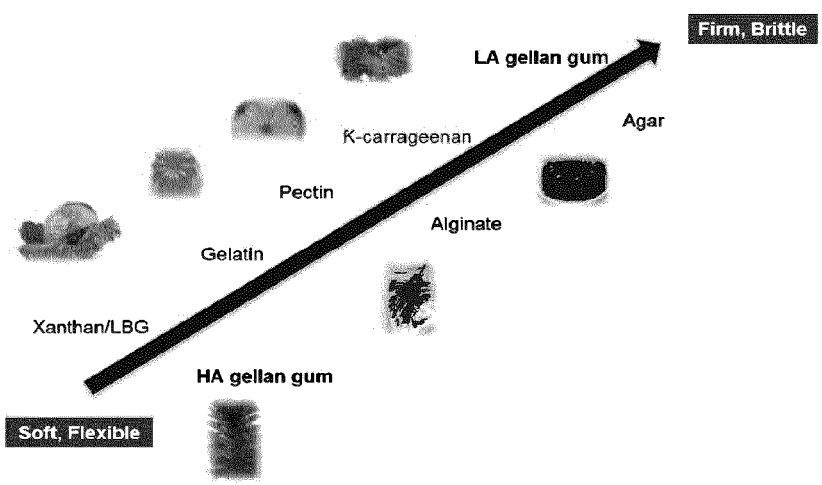

Since enzymes capable of deacylating gellan gum have not previously been described, screening for such an activity was conducted using a set of selected enzymes. Candidate esterase enzymes were selected based on 2 criteria; annotated or shown to be able to deacylate polysaccharides and/or synthesized from thermophilic microorganisms and known to possess activity at elevated temperatures (above high acyl gellan gum gelling temperature of about 70° C.).

Screening assays were conducted with increasing complexity. First, esterase activity was analysed using a general esterase substrate, 4-Nitrophenyl acetate, providing optimum pH and temperature for selected candidate enzymes. Secondly, enzymes were tested for activity on gellan gum that had been pre-degraded by ultrasonic treatment to avoid gelation of HA gellan gum during reactions. Analysis was done using acetic acid quantification by an UV-method (Megazymes, K-ACET) or by NMR. Finally, selected enzymes were tested for activity on rehydrated native gellan gum in which the acetate and glycerate remaining after enzymatic treatment were quantified. Thus, gellan gum was incubated with selected enzymes for a period of time and subsequently digested into smaller oligomers by hydrolysis. Levels of glycerate and acetate were determined using LC-MS on the oligomers.

A suitable esterase found in the screening procedure is one capable of deacetylating gellan gum, more specifically an acetyl esterase of the carbohydrate esterase family, in particular a pectin acetyl esterase.

The esterase may for instance be derived from a thermophilic microorganism and possesses enzyme activity at temperatures above about 40° C., preferably at temperatures in the range of 65° C.-80° C., such as a temperature of about 70-75° C. An example of such an esterase is a pectin acetyl esterase from *Clostridium thermocellum* (PAE12B, cat. nr. CZ00371, NZYtech).

In the present process, treatment with esterase may suitably be carried out at a pH in the range of 5.5-7.5, preferably a pH in the range of 6.0-7.0 such as a pH of 6.0-6.5. The temperature at which the esterase treatment is carried out is preferably in the range of 40-80° C., more preferably in the range of 60-75° C. such as in the range of 65-75° C. By way of example, the enzyme PAE12B has a broad temperature optimum with activity above 80° C., and can thus be used above the gelling temperature of high acyl gellan (about 70° C.).

A detailed analysis of optimal conditions for obtaining partially deacylated gellan gum using an enzymatic treatment with the esterase PAE12B was carried out. This made it possible to generate gellan gum samples with intermediate levels of acetate substitutions. The reaction conditions found to be optimal for enzymatic deacetylation using PAE 12B was pH 6.0-6.5, 70-75° C. Above this pH, chemical deacylation including glycerate hydrolysis took place, and below this pH, enzyme activity became negligible. Above this temperature, the enzyme activity became negligible and below this temperature, HA gellan gum formed a solid gel under conditions used.

Treatment with the esterase may be carried out by adding a sufficient amount of an esterase capable of partially deacylating gellan gum to a fermentation broth containing native gellan gum, wherein the esterase treatment is carried out for a sufficient period of time to effect partial deacylation of the gellan gum, e.g. a period of 10-1440 minutes. An amount of the esterase of 100-2000 units per L of fermentation broth has been found to be sufficient to effect partial deacylation which is preferably carried out for 60 minutes.

Native gellan gum may be produced by aerobic fermentation of a strain of *Sphingomonas elodea* (ATCC 31461) in a suitable aqueous growth medium containing suitable sources of carbon, nitrogen and inorganic salts. Suitable sources of carbon are sugars such as starch, fructose, glucose, sucrose, etc. Suitable sources of nitrogen are yeast hydrolysates, soybean meal, inorganic nitrogen etc. Suitable inorganic salts include sodium, potassium, calcium, ammonium, phosphate, magnesium sulphate etc.

Before the enzyme treatment, the fermentation broth may suitably be clarified by treatment with other types of enzymes such as a protease and a lysozyme.

After the esterase treatment, the partially deacylated gellan gum may be isolated from the fermentation broth by precipitation with an organic solvent such as an alcohol, for instance isopropanol or ethanol.

In an alternative embodiment, the esterase treatment is carried out after isolation of the gellan gum from the fermentation broth. In this embodiment, the esterase is added in an amount of 100-2000 units per g of the isolated gellan gum.

Figure 6:
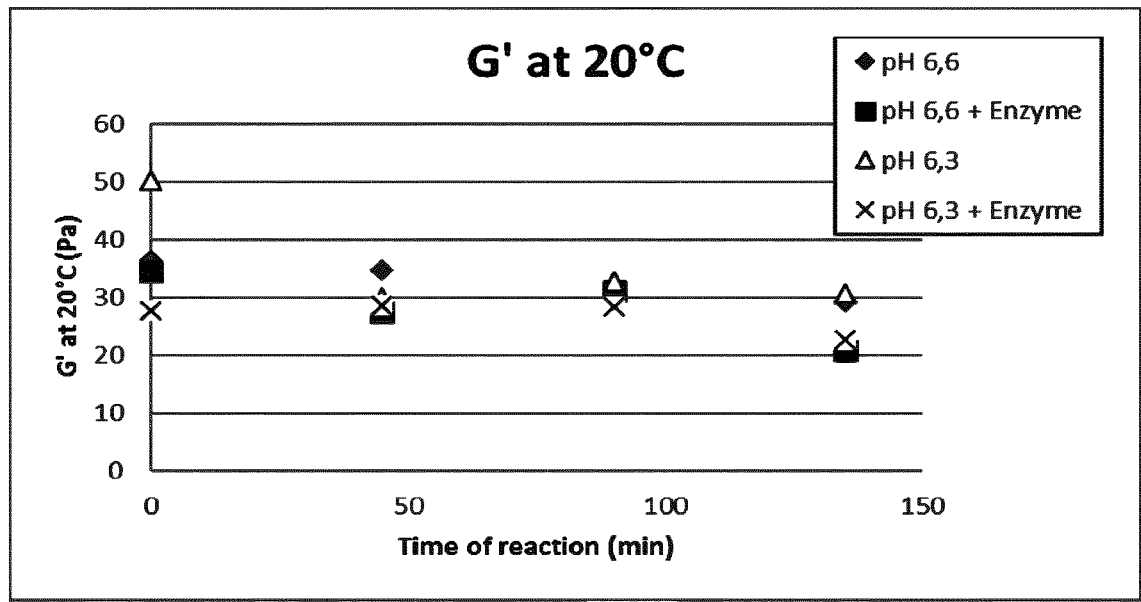
FIG. 6 is a plot of G' at 20° C. from gelling profiles of enzyme-treated (deacetylated) gellan gum compared to gellan gum that has not been treated with enzyme.

Partial deacetylation has been found to have an impact on the rheological properties of the gellan gum. A plot of G' at 20° C. from gelling profiles shows that at the longest reaction time the enzyme-treated samples have a lower viscosity (in Pa) compared to those that have not been treated with the enzyme, cf. FIG. 6. This indicates that the selective removal of acetate leads to a softer gel texture which may be advantageous in certain applications such as, for example, confectionary jellies, dessert gels, jams and jellies, bakery fillings and dairy desserts.

The changes in structure as a result of enzyme treatment has also been found to generate changes to the gelling temperature of gellan gum as determined by measuring the gelling profile of gellan gum before and after enzymatic deacylation. The gelling temperature of gellan increased during specific removal of acetate substitutions, showing an impact on gellan functional properties depending on the length of time of the enzymatic reaction, cf. FIG. 5 and Example 3 below. Increasing the gelling temperature increases the temperature at which a gel is formed and can therefore lead to stability at higher temperatures. This can be advantageous for higher filling temperatures in the final product. Also, a partially deacylated gellan gum with an increased gelling temperature has been found be capable of forming a fluid gel in liquids at low concentrations and may therefore advantageously be used to stabilize beverages that contain suspended particles of, for instance, proteins or insoluble minerals.

The partially deacylated gellan gum of the present invention has a molecular weight which is less than 10% reduced compared to the molecular weight of native gellan gum. This is an advantage because the molecular weight is important for gel strength and texture. These functional properties are important for the ability of gellan in providing the right stabilization of food products as gel formation is required to provide a network capable of suspending particulate components such as proteins or insoluble minerals.

In an embodiment, the invention relates to a partially deacylated gellan gum wherein between 0% and 48% of the repeating units of the polysaccharide chain comprise an acetate residue. Preferably, between 0% and 25%, more preferably between 0% and 10%, and even more preferably between 0.5% and 5%, of the repeating units of the poly-saccharide chain comprise an acetate residue.

In an embodiment, the invention relates to a partially deacylated gellan gum wherein between 0% and 48% of the repeating units of the polysaccharide chain comprise both a glycerate and an acetate residue. Preferably, between 0% and 25%, more preferably between 0% and 10%, and even more preferably between 0.5% and 5%, of the repeating units of the polysaccharide chain comprise both a glycerate and an acetate residue.

In an embodiment, the invention relates to a partially deacylated gellan gum wherein between 5% and 50% of the repeating units in the polysaccharide chain comprise neither an acetate not a glycerate residue. Preferably, between 10% and 30%, more preferably between 20% and 25%, of the repeating units of the polysaccharide chain comprise neither an acetate nor a glycerate residue.

In an embodiment, the invention relates to a partially deacylated gellan gum exhibiting a gelling temperature between 60° C. and 85° C., preferably between 70 and 80° C. The partially deacylated gellan gum according to this embodiment is considered to be particularly useful to stabilize beverages as it is capable of forming a fluid gel in liquids at low concentrations whereby particles present in the liquid are suspended.

The partially deacylated gellan gum may suitably be prepared by the inventive process disclosed herein.

The ability to create functionalities different from what is obtained by fully acylated or fully deacylated gellan gum generates new opportunities to use gellan in food products.

Thus, the partially deacylated gellan gum of the invention may be added as a gelling agent or texturant to food products such as selected from the group consisting of beverages, jams, jellies, bakery fillings, confections, dairy products, dessert gels, frostings, icings, glazes, low-fat spreads, micro-wavable foods, baked goods, puddings, sauces and dress-ings, structured foods and toppings to adjust the texture and viscosity thereof. The concentration of the partially deacy-lated gellan gum in food products may vary between 0.02% and 2% by weight depending on the desired texture and viscosity from a liquid (beverage) to a semisolid or solid (jellies and puddings). In a specific embodiment, the food product is a structured food product or gelled liquid intended to be ingested by patients suffering from dysphagia. Dyspha-gia is a condition in which a person has difficulty in swallowing. It is often managed by providing the patient with foods of specific viscosity and texture. By varying the texture of the gellan gum gels through partial deacetylation, a range of textures can be created that are suitable for the management of dysphagia.

In another aspect, the partially deacylated gellan gum of the invention may be added to pharmaceutical formulations such as a coating for tablets, to replace gelatin in hard and soft capsules, or as a thickener or gelling agent in gels, creams and lotions comprising one or more therapeutically active ingredients and appropriate excipients. The concen-tration of the partially deacylated gellan gum in the formu-lation is typically 0.02-2% by weight depending on the desired texture and/or viscosity from a liquid (e.g. lotion) to a semisolid (e.g. cream) or solid (e.g. tablet or capsule).

In a further aspect, the partially deacylated gellan gum may be added as a thickener or gelling agent to a personal care product such as toothpaste, liquid soap, shampoo, shower gel, cream, body lotion, body gel and deodorant gel. The concentration of the partially deacylated gellan gum in the formulation is typically 0.02-2% by weight depending on the desired texture and/or viscosity from a liquid (e.g. liquid soap) to a semisolid (e.g. cream, body lotion, sham-poo, toothpaste).

EXAMPLES

Example 1

HA gellan gum was prepared by aerobic fermentation of *Sphingomonas elodea* and isolated as described above.

Figure 3:
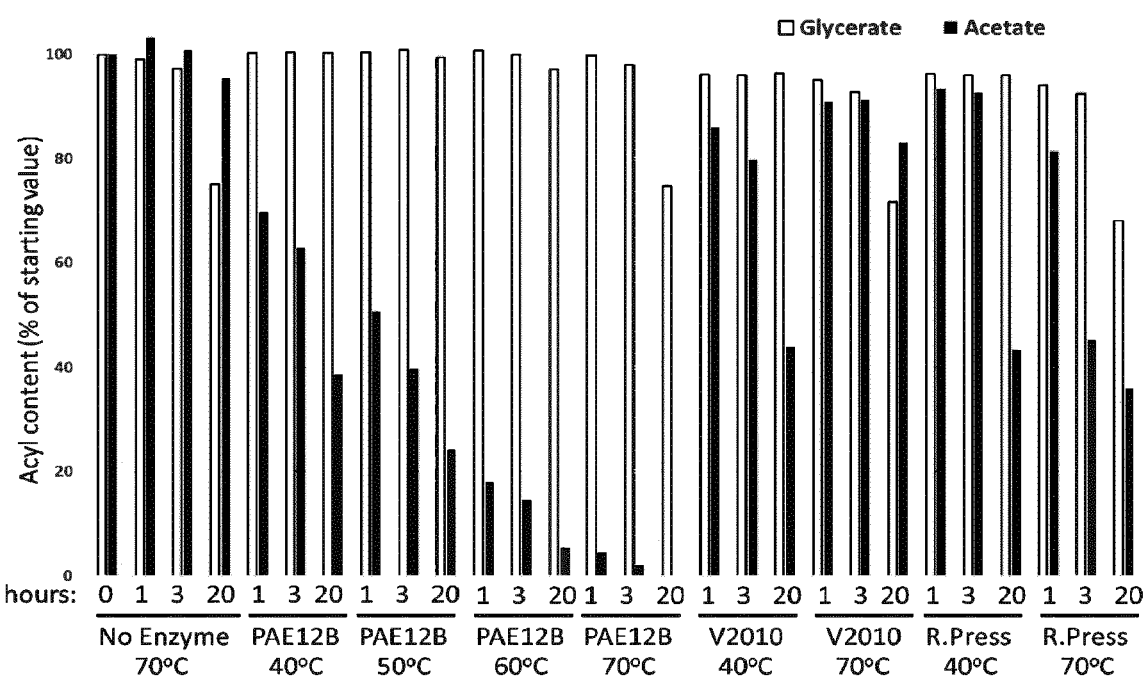
FIG. 3 is a bar graph showing the levels of acetate and glycerate remaining on the gellan after incubation of HA gellan gum at pH 6.3 and a temperature of 40-70° C. for 0, 1, 3 or 20 hours in the presence or absence of the enzymes PAE 12B, V2010 and Rapidase Press (abbreviated to R. Press).

The isolated HA gellan gum was incubated at pH 6.3 and between 40-70° C. alone or in combination with one of the enzymes PAE 12B (NZYtech), V2010 (Sigma) or Rapidase Press (DSM) in an amount of approximately 2000 esterase units per gram of gellan gum for different periods of time. Acetate and glycerate present on the gellan gum before and after the treatments was quantified as described above. As shown in FIG. 1c, there are 4 different repeating units (RU's) present in gellan gum. Theoretically, HA gellan consists of 50% RU1 and 50% RU2 and LA gellan gum consists of 100% RU4 corresponding to 1 glycerate per each RU (100% glycerate) and 1 acetate for every second RU (50% acetate). As shown in the bar graph (FIG. 3), the HA gellan gum used in this experiment contains approximately 80% glycerate and 45% acetate (0 hour). After incubation at pH 6.3, 70° C. for 1, 3 and 20 hours in the absence of enzyme, glycerate was slowly removed due to the slightly alkaline conditions whereas acetate levels remained almost unchanged. Incuba-tion with the esterase PAE 12B at pH 6.3 and at temperatures between 40-70° C. radically decreased the level of acetate. The effect was highest at 70° C. coinciding with the opti-mum temperature for this esterase. At 70° C., glycerate is removed at a rate similar to control conditions without esterase, but it was observed that under the experimental conditions used, enzymatic removal of acetate was much faster than chemical deacylation and it is possible to find optimal conditions in which acetate is removed enzymati-cally while the chemical de-acylation remains insignificant. Results show that the esterase PAE 12B specifically removes acetate from gellan gum and not glycerate. In addition, two different enzyme products, V2010 (Sigma) and Rapidase Press (R. Press, DSM) were found to be able to de-acetylate gellan gum, though at a slower rate than PAE 12B under the same conditions. The effect was highest after 20 hours of incubation at 40° C. for V2010 and after 20 hours of incubation at 40° C. and 70° C. for Rapidase Press, cf. FIG. 3.

Example 2

Figure 4A:
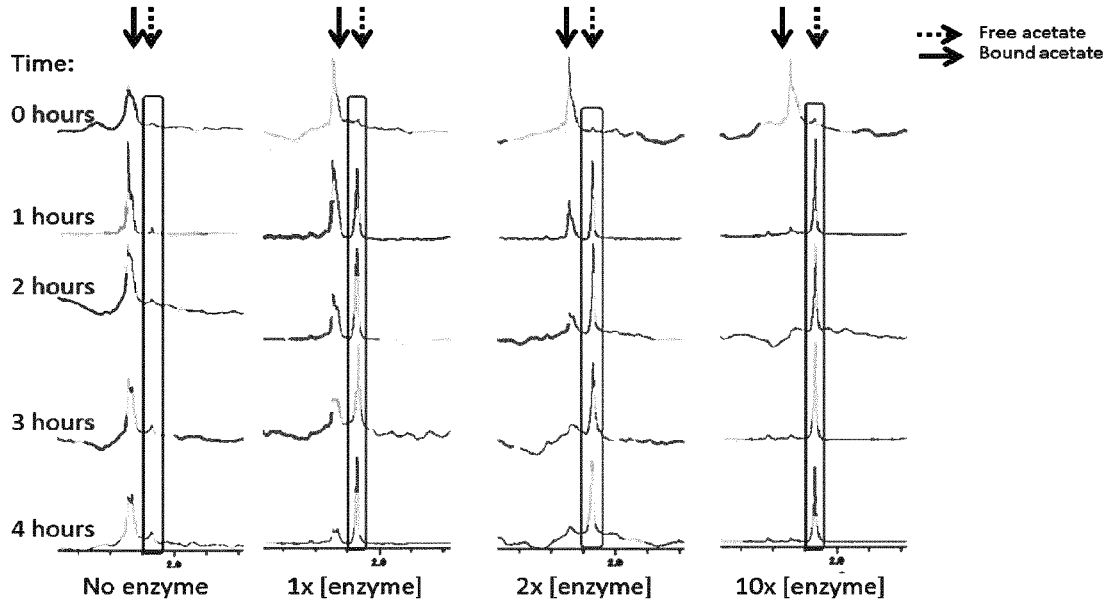
FIG. 4a shows the levels of bound and free acetate measured by NMR spectroscopy after incubation of HA gellan with the esterase PAE 12B for 0-4 hours at pH 6.6.
Figure 4B:
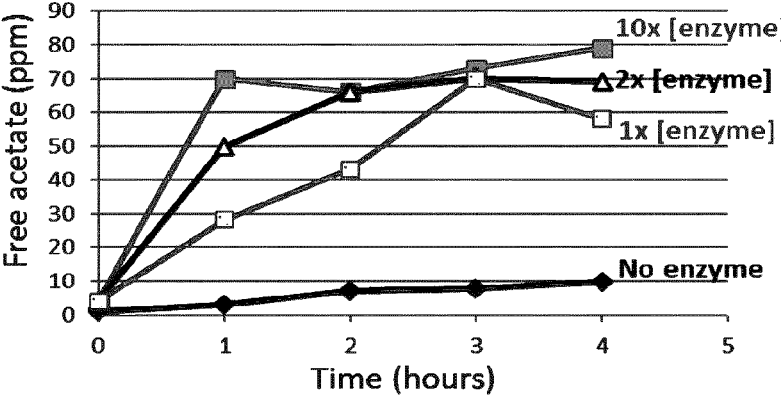
FIG. 4b is a graph showing the quantification of free acetate over time at different enzyme concentrations. In this figure, it is evident that different levels of deacetylation can be obtained using the PAE 12B enzyme.

Isolated HA gellan gum prepared as described in Example 1 was incubated with the esterase PAE 12B for 0-4 hours at pH 6.6, after which the amount of bound and free acetate was determined by NMR spectroscopy. The results are shown in FIG. 4a from which it appears that the enzymatic deacetylation progresses more quickly with increasing doses of enzyme under the experimental conditions used. The graph in FIG. 4b shows quantification of free acetate during the time of enzyme reaction, and the level of acetate removal can be controlled by adjusting the reaction time and enzyme dosage.

Example 3

Figure 5:
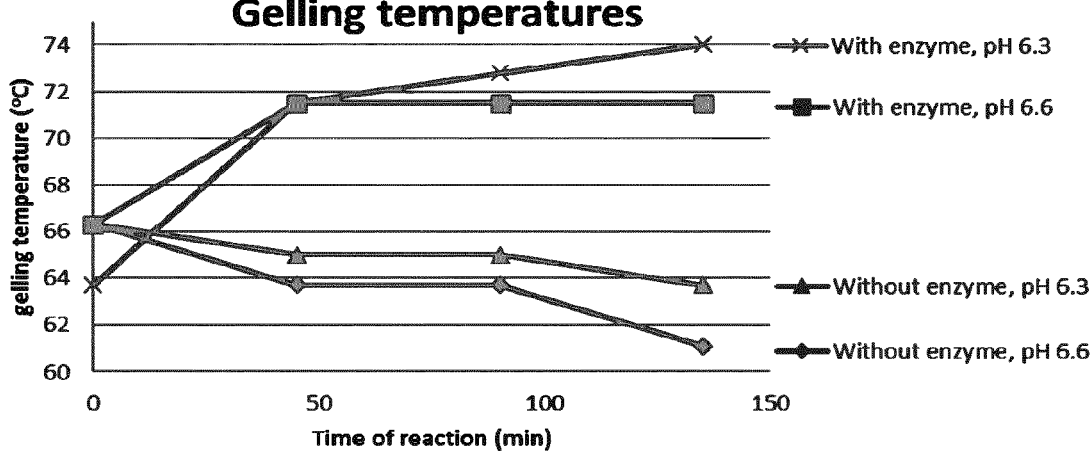
FIG. 5 is a graph showing changes in gelling temperature as a result of treatment of HA gellan with the esterase PAE 12B for 0, 45, 90 and 135 minutes.

Isolated HA gellan gum was incubated with the esterase PAE 12B under the same conditions as described in examples 1 and 2. The enzymatic reactions were stopped at different time points by decreasing the pH to a level in which PAE 12B has negligible activity. Then, the solutions were analysed by rheology providing a gelling profile and temperature. The results are shown in FIG. 5. When gellan gum was subjected to enzyme treatment, the gelling temperature was found to increase by 5-10° C. correlating with the simultaneous removal of acetate substitutions. A slower and smaller decrease in gelling temperature was observed for samples without enzyme correlating with the slow removal of glycerate under these conditions.

Partial deacetylation also has been shown to have an impact on the rheological properties of the gellan gum. A plot of G' at 20° C. from gelling profiles shows that at the longest reaction time the enzyme-treated samples have a lower viscosity (in Pa) compared to those that have not been treated with the enzyme, cf. FIG. 6. This indicates that the selective removal of acetate leads to a softer gel texture.

REFERENCES

Chandrasekaran R, Millane R P, Arnott S, 1988a, In Gums and Stabilizers for the Food Industry, p 183

Chandrasekaran R, Puigjaner L C, Joyce K L, Arnott S, 1988b, Carbohydrate Research, 181, 23.

Chandrasekaran R, Thailamabal V G, 1990, The influence of calcium ions, acetate and L-glycerate groups on the gellan double helix, Carbohydrate polymers, 12(4):431-442

Dreveton E, Monot F, Lecourtier J, Ballerini D, Choplin L (1996) Influence of fermentation hydrodynamics on gellan gum physico-chemical characteristics, journal of fermentation and bioengineering, 82, 3, 272-216.

Fialho A M, Martins L O, Donval M L, Leitao J H, Ridout M J, Jay A J, Morris V J, Sa-Correia 1, 1999, Structures and Properties of Gellan Polymers Produced by Sphingomonas paucimobilis ATCC 31461 from Lactose Compared with Those Produced from Glucose and from Cheese Whey, applied and environmental microbiology, 65, 6, 2485-2491

Jaya A J, Colquhouna I J, Ridouta M J, Brownsey G J, Morrisa V J, Fialho A M, Leitão H J, S5-Correia I (1998) Analysis of structure and function of gellans with different substitution patterns, Carbohydrate Polymers 35, 179-188

Kool M M, Gruppen H, Sworn G, Schols H A, 2013, Comparison of xanthans by the relative abundance of its six constituent repeating units, Carbohydrate polymers, 98 (2013) 914-921

Morrison N A, Clark R C, Chen Y L, Talashek T, Sworn G, 1999, Gelatin alternatives for the food industry, Progr Colloid Polym Sci (1999) 114: 127±131

Morris E R, Gothard M G E, Hember M W N, Manning C E, Robinson G, 1996, Conformational and Rheological Transitions of Welan, Rhamsan and Aacylated Gellan, Carbohydrate Polymers, 30 (1996) 165-175

Remoroza C A, Buchholt H C, Gruppen H, Schols H A, 2014, Descriptive parameters for revealing substitution patterns of sugar beet pectins using pectolytic enzymes, Carbohydrate Polymers, 101:1205-15

The invention claimed is:

1. A process for preparing partially deacylated gellan gum by enzymatic treatment, wherein the process comprises:
   subjecting native or high acyl gellan gum in a fermentation broth to treatment with an esterase that partially deacylates gellan gum, and
   isolating a partially deacylated gellan gum from the fermentation broth after the esterase treatment.

2. The process of claim 1, wherein the process comprises subjecting native or high acyl gellan gum for removing acetate at a pH in the range of 5.5 to 7.5 at a temperature in the range of 40-80° C. and isolating a partially deaceylated gellan gum from the fermentation broth after treatment with the esterase.

3. The process of claim 1, wherein the esterase is pectin acetyl esterase 12B derived from Clostridium thermocellum.

4. The process of claim 1, wherein the esterase treatment is carried out at a pH in the range of 5.5-7.5.

5. The process of claim 1, wherein the esterase treatment is carried out at a temperature in the range of 40-80° C.

6. The process of claim 1, wherein the amount of esterase is 100-2000 units per L of fermentation broth.

7. The process of claim 1, wherein the esterase treatment is carried out for 10-1440 minutes.

8. The process of claim 1, wherein the esterase treatment is carried out at a pH in the range of 6.0-6.5.

9. The process of claim 1, wherein the esterase treatment is carried out at a temperature in the range of 65-75° C.

10. The process according to claim 1, wherein the treatment with the esterase produces the partially deacylated gellan gum to have a glycerate concentration ranging from 70 percent to 100 percent of an original glycerate concentration present in the native or high acyl gellan gum before enzymatic treatment.

11. The process of claim 1, wherein the esterase is an acetyl esterase of the carbohydrate esterase family or a pectin acetyl esterase.

* * * * *